US011596755B2

(12) United States Patent
Takatori et al.

(10) Patent No.: US 11,596,755 B2
(45) Date of Patent: Mar. 7, 2023

(54) PATIENT TREATMENT SYSTEM AND MONITORING DEVICE

(71) Applicant: NIHON KOHDEN CORPORATION, Tokyo (JP)

(72) Inventors: Fumihiko Takatori, Tokorozawa (JP); Masayuki Inoue, Tokorozawa (JP); Kazumasa Ito, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 814 days.

(21) Appl. No.: 16/380,521

(22) Filed: Apr. 10, 2019

(65) Prior Publication Data

US 2019/0328987 A1   Oct. 31, 2019

(30) Foreign Application Priority Data

Apr. 27, 2018   (JP) .............................. JP2018-087334

(51) Int. Cl.
*A61M 16/00* (2006.01)
*A61M 16/06* (2006.01)
*A61B 5/024* (2006.01)
*A61B 5/00* (2006.01)
*A61B 5/318* (2021.01)

(52) U.S. Cl.
CPC ........... *A61M 16/024* (2017.08); *A61B 5/024* (2013.01); *A61B 5/318* (2021.01); *A61B 5/742* (2013.01); *A61M 16/0003* (2014.02); *A61M 16/0078* (2013.01); *A61M 16/0081* (2014.02); *A61M 16/06* (2013.01); *A61B 2503/045* (2013.01); *A61M 2205/3303* (2013.01); *A61M 2240/00* (2013.01)

(58) Field of Classification Search
CPC ............ A61M 16/024; A61M 16/0078; A61M 16/0081
See application file for complete search history.

(56) References Cited

U.S. PATENT DOCUMENTS

| 2014/0275820 A1* | 9/2014 | Varga ................... A61B 5/0022 600/301 |
| 2015/0018694 A1* | 1/2015 | Gomo .................... A61B 5/742 600/484 |
| 2016/0166795 A1* | 6/2016 | Belsinger, Jr. ...... A61M 16/205 128/203.27 |

(Continued)

FOREIGN PATENT DOCUMENTS

| JP | 2017-055965 A | 3/2017 |
| JP | 2019-188030 A | 10/2019 |

OTHER PUBLICATIONS

Japanese Office Action dated Sep. 5, 2022 issued in Japanese Patent Application No. 2021-167138.

*Primary Examiner* — Margaret M Luarca
(74) *Attorney, Agent, or Firm* — Pearne & Gordon, LLP (57) ABSTRACT

A patient treatment system includes a ventilation bag, and a monitoring device which is configured so as to be connectable to the ventilation bag. The monitoring device measures the pulse rate derived from the heart rate of a neonate, from signals of ECG electrodes which are connected to the monitoring device. In a case where an abnormality of measurement information of the pulse rate is detected, the monitoring device notifies of first information prompting ventilation by the ventilation bag.

14 Claims, 8 Drawing Sheets

(56) References Cited

U.S. PATENT DOCUMENTS

| | | |
|---|---|---|
| 2017/0266399 A1 | 9/2017 | Campana et al. |
| 2018/0368762 A1* | 12/2018 | Pirtini Cetingul .. A61M 16/022 |
| 2019/0328987 A1 | 10/2019 | Takatori et al. |

* cited by examiner

| | FIRST PARAMETER | SECOND PARAMETER | THIRD PARAMETER | INDICATOR 25 |
|---|---|---|---|---|
| CASE 1 | NORMAL | — | — | LIGHTING/BLINKING IS NOT PERFORMED |
| CASE 2 | ABNORMAL | NORMAL | NORMAL | LIGHT UP IN BLUE |
| CASE 3 | ABNORMAL | NORMAL | ABNORMAL | LIGHT UP IN ORANGE |
| CASE 4 | ABNORMAL | ABNORMAL | NORMAL | LIGHT UP IN YELLOW |
| CASE 5 | ABNORMAL | ABNORMAL | ABNORMAL | LIGHT UP IN RED |

PATIENT TREATMENT SYSTEM AND MONITORING DEVICE

CROSS-REFERENCE TO RELATED APPLICATIONS

This application is based on and claims priority under 35 USC 119 from Japanese Patent Application No. 2018-087334 filed on Apr. 27, 2018, the contents of which are incorporated herein by reference.

TECHNICAL FIELD

The presently disclosed subject matter relates to a patient treatment system and a monitoring device.

BACKGROUND ART

In hypoventilation or respiratory arrest, a resuscitation bag which is called an Ambu bag or a Jackson Rees bag is widely used. A rescuer causes a mask of a resuscitation bag to cover an area of a subject extending from the oral cavity to the nasal cavity, and presses the resuscitation bag connected to the mask, to perform ventilation.

Patent Literature 1 discloses a technique relating to ventilation using a resuscitation bag. A respiratory condition display apparatus disclosed in Patent Literature 1 calculates normal or abnormal values of respiratory parameters during ventilation, based on physical indices (the body weight, the age, the sex, and the like), and displays together measurement values and normal values (or abnormal values) of the respiratory parameters.

CITATION LIST

Patent Literature

Patent Literature 1: JP-A-2017-055965

SUMMARY OF INVENTION

As necessary, a neonate who has been just born is subjected to rapid emergency treatment after the body condition is adequately known. In order to perform rapid emergency treatment, it is more desirable to manage the condition of the neonate with consideration of also parameters other than those relating to the respiration. This problem occurs not only in a neonate, but also in an infant.

In view of the circumstances, it is an object of the presently disclosed subject matter to provide a patient treatment system and monitoring device which enable the condition of a patient to be more correctly managed.

A mode of the patient treatment system of the presently disclosed subject matter is a neonatal treatment system including a ventilation medical apparatus, and a monitoring device which is configured so as to be connectable to the ventilation medical apparatus, wherein the monitoring device measures a first parameter derived from a heart rate of a neonate, from a signal of a first sensor which is connected to the monitoring device, and, in a case where an abnormality of measurement information of the first parameter is detected, notifies of first information prompting ventilation by the ventilation medical apparatus.

According to the configuration, in the case where the first parameter derived from the heart rate is abnormal, notification prompting ventilation is performed. In the case where the measurement information of the first parameter is abnormal, ventilation is prompted, whereby ventilation can be started at an adequate timing. Since ventilation is started at an adequate timing, the condition of a patient can be more correctly managed.

According to the presently disclosed subject matter, it is possible to provide a patient treatment system and monitoring device which enable the condition of a patient to be more correctly managed.

DESCRIPTION OF EMBODIMENTS

Figure 1:
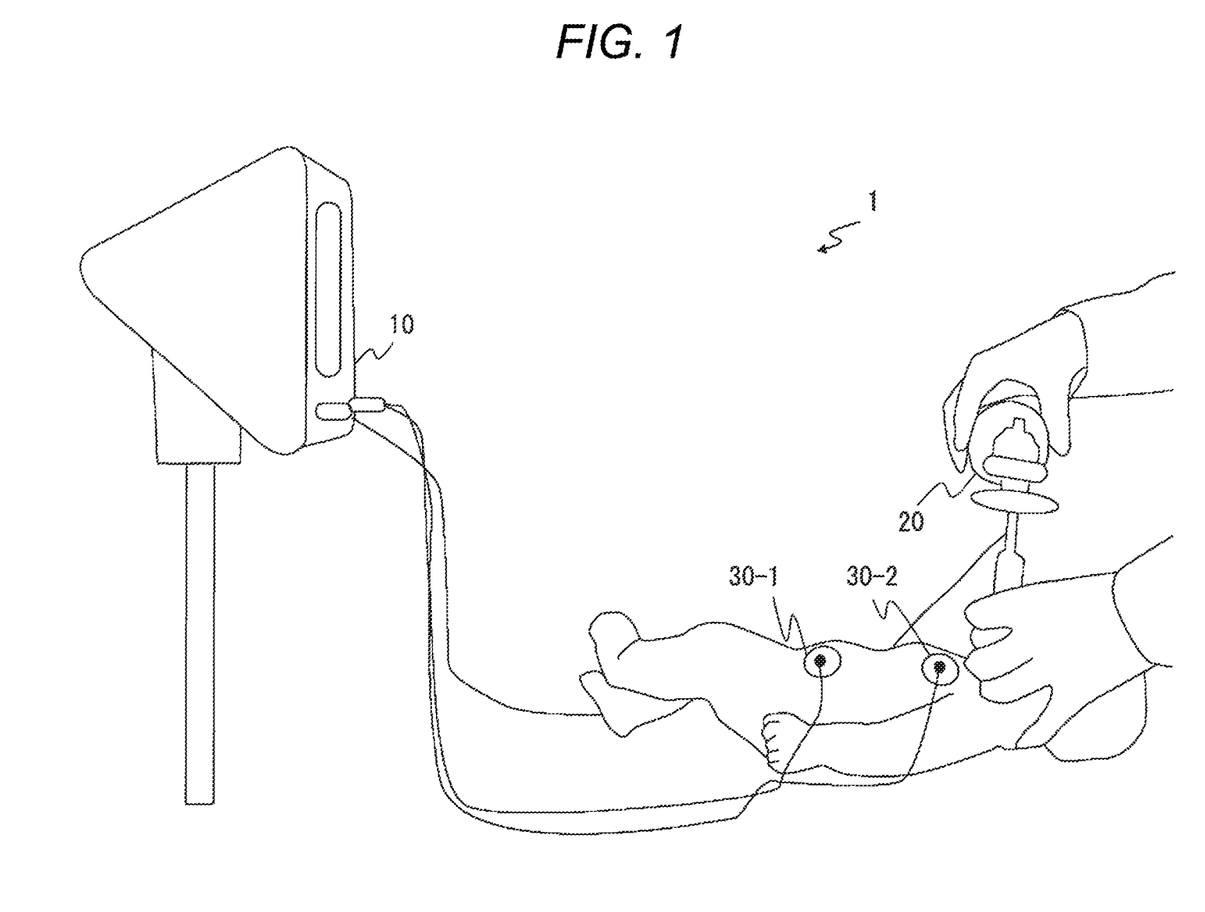
FIG. 1 illustrates the configuration of a neonate treatment system 1 of Embodiment 1.

Hereinafter, an embodiment of the presently disclosed subject matter will be described with reference to the drawings. FIG. 1 illustrates the configuration of a neonate treatment system 1 of the embodiment. The neonate treatment system 1 may include a monitoring device 10, and a ventilation bag 20 which is detachably attached to the monitoring device 10. The neonate treatment system 1 is a mode of the patient treatment system which is used in management of the condition of a patient, and particularly effective in management of the condition of a neonate. The neonate treatment system 1 is particularly useful in, for example, respiratory management which is started from the birth of a neonate.

The monitoring device 10 can be deemed as equivalent to a simple patient monitor, and connected with various vital signs sensors (such as ECG electrodes, a child cuff, and a body temperature probe) via connectors. The monitoring device 10 acquires vital signs signals from the vital signs sensors to acquire measurement information (measurement waveforms and values of the blood pressure, the heart rate, an ECG, the body temperature, the arterial oxygen saturation, and the like) of various vital signs from the vital sings signals. In the embodiment, the monitoring device 10 is connected with ECG electrodes 30-1 to 30-N, and the ventilation bag 20. The ECG electrodes 30-1 to 30-N are examples of the sensor (the first sensor) for acquiring measurement information of a heart rate-derived parameter (for example, the pulse rate, and this will be referred to also as the first parameter). Although, in the embodiment, the monitoring device 10 is wire connected to the ECG electrodes 30-1 to 30-3 (in the following description, in the case where the electrodes 30-1 to 30-3 are not particularly distinguished from each other, the electrodes will be denoted to simply by 30), and the ventilation bag 20, a configuration may be employed where various kinds of information are acquired by wireless communication connection from the ECG electrodes 30 (the first sensor) and the ventilation bag 20. The number of the ECG electrodes 30 which are connected to the monitoring device 10 may be arbitrary.

Figure 2:
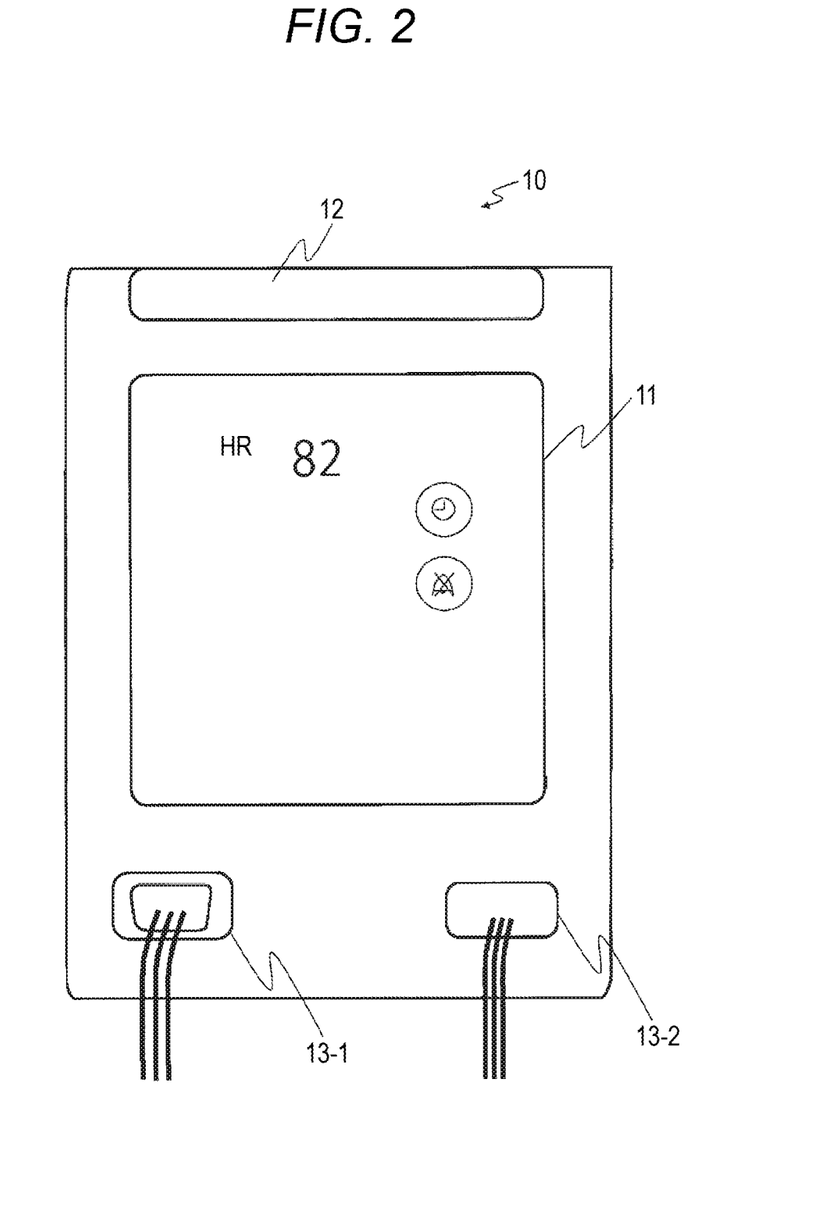
FIG. 2 is an external view of a monitoring device 10 of Embodiment 1, as viewed from the front side.

FIG. 2 illustrates an image which is obtained by viewing the monitoring device 10 from the front side. As illustrated in FIG. 2, the monitoring device 10 has, on the housing, a display 11, and an indicator 12 (the second indicator). The monitoring device 10 may further have connectors 13-1, 13-2 which are connected with the ECG electrodes 30 and the ventilation bag 20.

The display 11 is a so-called liquid crystal display, and may be a touch display which can be operated by the user (medical person). Measurement values and waveforms, and the like of various vital signs can be displayed on the display 11.

The indicator 12 is, for example, an LED lamp, and blinks or lights up in accordance with the skillfulness of bag ventilation by the ventilation bag 20, and normalities/abnormalities of various vital signs. The blinking and lighting operations of the indicator 12 will be described in detail later with reference to FIGS. 5A to 5E, etc.

The monitoring device 10 may include the connectors 13-1, 13-2 which are to be connected with vital signs sensors (in the following description, in the case where the connectors 13-1, 13-2 are not particularly distinguished from each other, the connectors will be referred to simply as the connectors 13). In the embodiment, the connector 13-1 is connected with the ECG electrodes 30-1 to 30-3, and the connector 13-2 is connected with the ventilation bag 20. The number of the connectors 13 which are disposed in the monitoring device 10 may be arbitrary.

Figure 3:
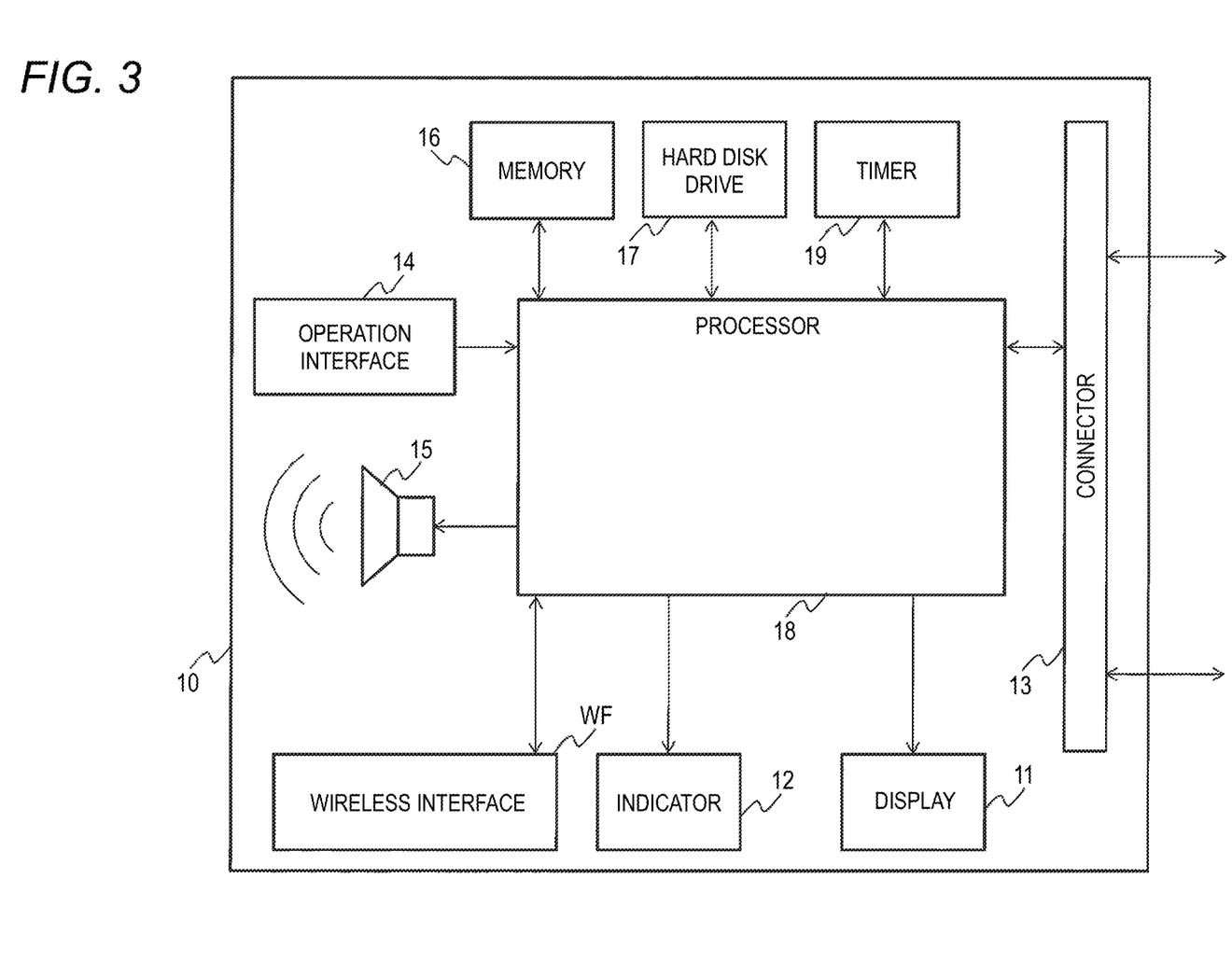
FIG. 3 is a block diagram illustrating the electrical configuration of the monitoring device 10 of Embodiment 1.

The electrical configuration of the monitoring device 10 will be described with reference to FIG. 3. FIG. 3 is a block diagram illustrating the electrical configuration of the monitoring device 10.

The monitoring device 10 may include the display 11, the indicator 12, the connectors 13, an operation interface 14, a speaker 15, a memory 16, a hard disk drive 17, a processor 18, and a timer 19. The monitoring device 10 may further include a wireless interface WF for wireless communication. The wireless interface WF is an interface for transmitting and receiving data to and from an arbitrary other device, and enables, for example, data communication according to a wireless LAN standard.

As described above, the connectors 13 are interfaces for connecting with the ECG electrodes 30 and the ventilation bag 20. The connectors 13 supply signals received from the ECG electrodes 30 and the ventilation bag 20, to the processor 18.

The user (mainly, a medical person such as the doctor or the nurse) operates the operation interface 14 to perform various input operations. The operation interface 14 is configured by buttons, knobs, a rotary selector, keys, or the like which are disposed on, for example, the housing of the monitoring device 10. As described above, the operation interface 14 may be integrated with the display 11 (namely, configured as a touch display). An example of the operation interface 14 is a start button for monitoring or an alarm cancellation button. An input through the operation interface 14 is supplied to the processor 18.

The speaker 15 outputs various notification sounds such as an alarm sound. The speaker 15 performs notification under control of the processor 18.

The memory 16 is primary storage means which functions as a working area when the processor 18 executes a program. The hard disk drive 17 stores various programs (including a system software and various application software) and data (such as pulse rate information). The hard disk drive 17 may be incorporated in the monitoring device 10, or externally disposed.

The processor 18 (the controller) controls the operation of the monitoring device 10. Specifically, the processor 18 performs: a measurement process based on the signals acquired from the ventilation bag 20 and the ECG electrodes 30; recording of measurement information (measurement waveforms and values) of the vital signs in the hard disk drive 17; control of a display on the display 11; control of lighting/blinking of the indicator 12; control of outputting a sound from the speaker 15; and the like. Moreover, the processor 18 transmits an instruction signal to the ventilation bag 20, thereby controlling blinking and lighting up operations of an indicator 25 (the first indicator) of the ventilation bag 20 which will be described later.

The process of the processor 18 is realized by developing and executing a program which is read from the hard disk drive 17, on the memory 16. The control of a display on the display 11, that of lighting/blinking of the indicator 12, and that of outputting a sound from the speaker 15 will be specifically described later with reference FIGS. 5A to 5E.

The programs may be stored by using a non-transitory computer readable medium of any one of various types, and then supplied to a computer. The non-transitory computer readable medium includes tangible storage media of various types. Examples of the non-transitory computer readable medium are a magnetic recording medium (for example, a flexible disk, a magnetic tape, and a hard disk drive), a magneto-optical recording medium (for example, a magneto-optical disk), a CD-ROM (Read Only Memory), a CD-R, a CD-R/W, a semiconductor memory (for example, a mask ROM, a PROM (Programmable ROM), an EPROM (Erasable PROM), a flash ROM, and a RAM (random access memory)). Alternatively, the programs may be supplied to the computer by means of a transitory computer readable medium of any one of various types. Examples of the transitory computer readable medium include an electrical signal, an optical signal, and an electromagnetic wave. The transitory computer readable medium can supply the programs to the computer through a wired communication path such as an electric wire or an optical fiber, or a wireless communication path.

A part of processes of the processor 18, and peripheral processes may be realized by electronic circuits which are not illustrated. The processes of the processor 18, such as display of vital signs are performed in the same or similar manner as those in a usual patient monitor.

The timer 19 measures the time under control of the processor 18. For example, the timer 19 measures the time in accordance with pressing of the start button.

Figure 4:
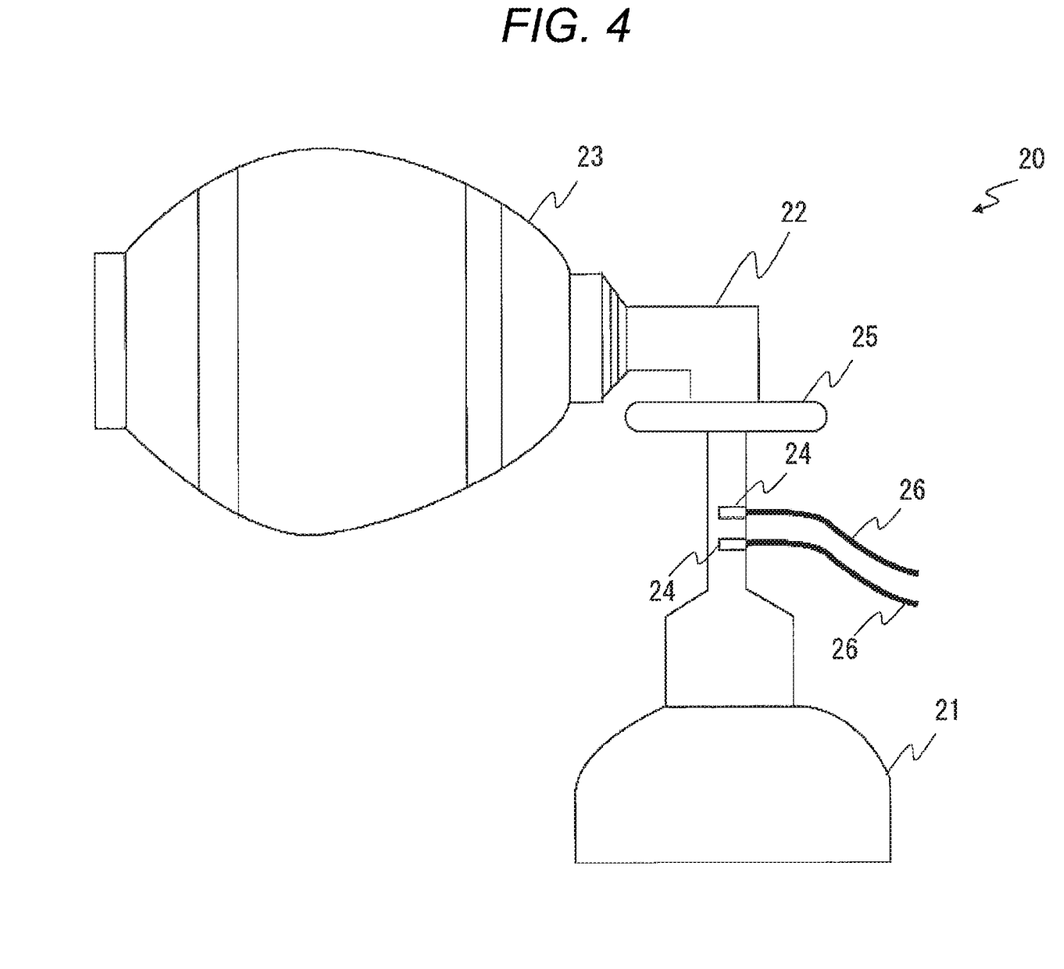
FIG. 4 is an external view illustrating the configuration of a ventilation bag 20 in Embodiment 1.

Then, the configuration of the ventilation bag 20 will be described with reference to FIGS. 1 and 4. Together with this, also techniques for calculating various parameters by the processor 18 will be described. The ventilation bag 20 may have a flexible mask portion 21, a flow path 22, and a bag 23. The ventilation bag 20 is one kind of ventilation medical apparatus which applies positive pressure ventilation on a neonate. Examples of the ventilation bag are an Ambu bag and a Jackson Rees bag. In a ventilation medical apparatus, positive pressure ventilation in the patient such as a neonate is performed manually or automatically (semi-automatically). An example of the ventilation medical apparatus is a concept including a T-piece connected to a pressure source, or a respirator. In the following, the description will be made assuming that the ventilation bag 20 is a so-called Ambu bag.

The flexible mask portion 21 is a portion which is to be contacted with an area of the rescuee such as a neonate extending from the oral cavity to the nasal cavity. The bag 23 is an air bag which is to be pressed by the user (medical person). When the user presses the bag 23, the bag deflates, and the air is sent into the flexible mask portion 21 through the flow path 22.

The flow path 22 is a flow path through which, when the bag 23 is pressed, the air is sent from the bag 23 into the flexible mask portion 21. A backflow valve and a hepafilter may be disposed in the flow path 22.

The flow path 22 may include a sensor 24 (the second sensor) and the indicator 25 (the first indicator). The sensor 24 acquires information of a fluid (gas) flowing through the flow path 22, and may be a flow sensor or a pressure sensor.

The indicator 25 and the sensor 24 are configured so as to able to transmit and receive data (signals) to and from the monitoring device 10. In the embodiment, the ventilation bag 20 transmits and receives data to and from the monitoring device 10 via cables 26. The monitoring device 10 and the ventilation bag 20 may be configured so as to be able to transmit and receive data by wireless communication. In this case, the ventilation bag 20 may include a battery, a control device (a processor, a memory, and a storage device), and the like, and have a wireless communication function. In the case where the monitoring device 10 and the ventilation bag 20 are wire connected to each other, a power source may be supplied from the monitoring device 10 to the ventilation bag 20.

Although, in the embodiment, it is assumed that the sensor 24 is configured by both a flow sensor and a pressure sensor, the sensor may be configured by only one of the two sensors, or by another kind of sensor. The flow sensor acquires the amount of air flowing toward the subject, and that of air flowing out from the side of the subject. The pressure sensor acquires information of the degrees of the pressures of the inspiration and the expiration. The information is supplied to the processor 18 of the monitoring device 10 via the cables 26.

The above-described processor 18 calculates measurement information of a parameter (referred to also as a second parameter) relating to bag ventilation, by using the information of the air amount, and that of the degrees of the pressures, or measurement information of a parameter (referred to also as a third parameter) relating to respiration of a neonate. Examples of the parameter relating to bag ventilation are the leak rate and the ventilation rate. Examples of the parameter relating to respiration are the PIP (Peak Inspiratory Pressure) and the PEEP (Positive End-Expiratory Pressure).

For example, the processor 18 calculates the difference between the amount of the air flowing toward the subject, and that of the air flowing out from the side of the subject, and further calculates the leak rate which indicates the rate of air leaking from the flexible mask portion 21, based on the difference. In the same or similar manner, the processor 18 calculates the ventilation rate and the ventilation amount from the information of the flow sensor, by using techniques which are employed in the field of usual bag/mask ventilation.

The processor 18 further calculates the PIP and the PEEP by using pressure information. The processor 18 may calculate the values of the PIP and the PEEP based on whether the pressure is due to the expiration or not, and the degree of the pressure, by using known techniques.

Alternatively, the sensor 24 may acquire information for calculating the partial pressure of carbon dioxide in the so-called expiration. The processor 18 calculates a so-called capnogram by using the information and a known technique.

The processor 18 may detect airway blockage (one kind of conditions of a neonate) of a neonate by using the air flow information acquired by the flow sensor, and the pressure information of the pressure sensor. For example, the processor 18 may detect airway blockage by an arbitrary comparison process in which both the expiration amount and the detected pressure are used.

The sensor 24 is not required to be disposed in the flow path 22, and may be disposed in the flexible mask portion 21.

The indicator 25 is, for example, an LED lamp, and configured so as to be able to light up, blink, and light off in accordance with an instruction signal supplied from the monitoring device 10. The indicator 25 notifies of information (the second information) relating to the skillfulness of bag ventilation by the ventilation bag 20, by means of blinking or lighting up.

Then, a specific operation example of the neonate treatment system 1 will be described with reference to FIGS. 5A to 5E. In the description of FIGS. 5A to 5E, the operation of the monitoring device 10 is controlled mainly by the processor 18.

In the case where a neonate is born, the neonate treatment system 1 performs operations of supporting an appropriate respiration management and the like. It is widely known that, in the case where a neonate is born, when the neonate does not cry or breathe within about 20 seconds of the birth, it is desirable to perform manual ventilation.

Figure 5A:
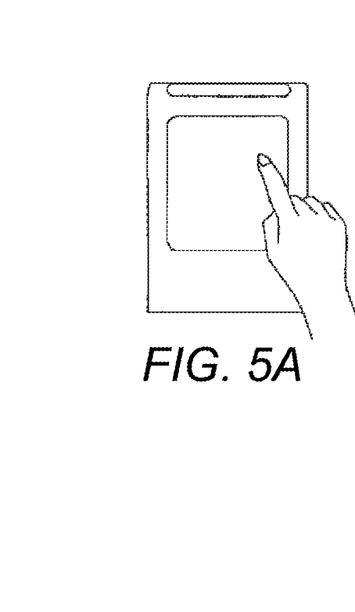
FIGS. 5A to 5E illustrate specific operation examples of the neonate treatment system 1 of Embodiment 1.

At the timing when a neonate is born, therefore, the user (medical person) executes a start event (FIG. 5A). In the embodiment, the start event is an operation in which the user presses the start button that is one kind of the operation interface 14. The monitoring device 10 measures a given period of time (for example, 20 seconds) after the execution of the start event.

The user may manually measure the given period of time by using a stopwatch or the like. However, it is preferred to manage the condition of a neonate together with the elapsed time period after the birth of the neonate, and therefore a mode in which the above-described start event is executed is more preferred.

Figure 5B:
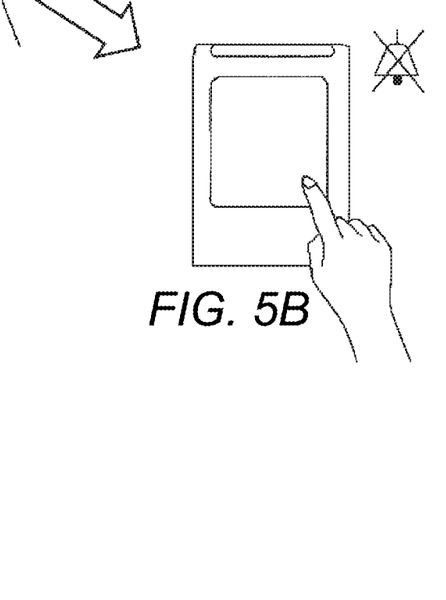

When the neonate starts to cry or breathe, the user presses a stop button (one kind of the operation interface 14) (FIG. 5B). The pressing of the stop button is one kind of an inputting operation for notifying that the neonate is normal. When the stop button is pressed before passage of the given period of time, the monitoring device 10 ends the time measurement.

Figure 5C:
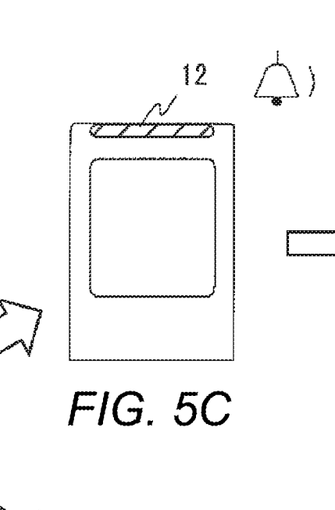

When the stop button is not pressed even after passage of the given period of time from the birth of the neonate, by contrast, the monitoring device 10 performs a notification prompting measurement of a vital sign parameter (the first parameter) derived from the heart rate of the neonate (FIG. 5C). In the example described below, it is assumed that the vital sing parameter derived from the heart rate of the neonate is the pulse rate.

For example, the processor 18 may cause the display 11 to perform a display for prompting attachment of the ECG electrodes 30, or the indicator 12 to light up in blue (the color indicating attachment of the ECG electrodes 30) (in FIG. 5C, slant hatching). Moreover, the processor 18 may transmit an instruction signal instructing the indicator 25 to light up in a predetermined color. Furthermore, the processor 18 may output an alarm sound (the first alarm sound) for prompting application of the ECG electrodes 30, from the speaker 15 (FIG. 5C).

The indicators 12, 25 are not required to light up, but to blink. The lighting/blinking may be performed in an arbitrary color.

In accordance with the notification prompting measurement of the pulse rate, the user applies the ECG electrodes 30 to the neonate. The processor 18 measures the pulse rate based on the vital signs signals acquired from the ECG electrodes 30, and causes the display 11 to display the measured pulse rate. The measurement of the pulse rate is desired to be performed for about 8 to 13 seconds.

The processor 18 compares the measured pulse rate with a predetermined threshold (in the following description, 60), and, if the pulse rate is 60 or more (the pulse rate is normal), ends the notification prompting measurement of the pulse rate (for example, lighting up of the indicators 12, 25).

Figure 5D:
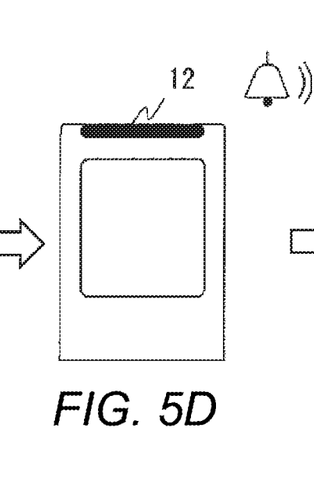

If the pulse rate is smaller than 60, by contrast, the monitoring device 10 notifies of information (the first information) prompting bag ventilation in which the ventilation bag 20 is used (FIG. 5D). For example, the processor 18 may change the blue lighting of the indicator 12 to yellow lighting. Moreover, the processor 18 may transmit an instruction signal for changing the blue lighting of the indicator 25 to yellow lighting, to the ventilation bag 20, thereby changing the lighting color of the indicator 25. Furthermore, the processor 18 may cause the display 11 to display a message of "Perform bag ventilation."

In the same or similar manner, the processor 18 may output an alarm sound (the second alarm sound) for prompting bag ventilation, from the speaker 15 (FIG. 5D). When the alarm sound (the first alarm sound) for prompting application of the ECG electrodes 30 is differentiated from the alarm sound (the second alarm sound) for prompting bag ventilation, it is possible to clearly notify of a situation where the neonate must be treated, or that where a next action is required.

Of course, the processor 18 may notify of information prompting bag ventilation by using a combination of the display on the display 11, the lighting/blinking of the indicator 12 and/or the indicator 25, and the output from the speaker 15.

After the notification prompting bag ventilation, the processor 18 acquires sensing information which is acquired by the sensor 24 disposed in the ventilation bag 20. The sensing information is, for example, information (a signal) acquired by the pressure sensor, and information (a signal) acquired by the flow sensor. The processor 18 calculates, from these sets of information, measurement information (measurement values and waveforms) of parameters relating to bag ventilation. The parameters relating to bag ventilation include, for example, the ventilation rhythm (number of manual ventilations/minute), the leak rate (the rate of the leaking amount to the air supply amount), and the like.

The processor 18 further calculates measurement information (measurement values and waveforms) of parameters relating to respiration of the subject from sensing information of the sensor 24. Examples of the parameters relating to respiration are the PIP and PEEP which are described above, occurrence of airway blockage, and the partial pressure of carbon dioxide in the expiration.

The processor 18 detects the information (the second information) relating to the skillfulness of the bag ventilation by the ventilation bag 20 based on the parameter (the second parameter) relating to bag ventilation. For example, the processor 18 calculates the information relating to the skillfulness of bag ventilation from a measurement value relating to the mask leak, that of the ventilation rhythm, and the like. The information indicating the skillfulness of bag ventilation has, in the simplest case, two values of "The technique for bag ventilation is normal" and "It is necessary to improve the technique for bag ventilation." When at least one of the ventilation rhythm and the leak amount is abnormal, for example, the processor 18 calculates "It is necessary to improve the technique for bag ventilation" as the information indicating the skillfulness of bag ventilation. An abnormality of the ventilation rhythm or the leak amount may be detected, for example, by comparing the measurement value with the threshold.

Figure 5E:
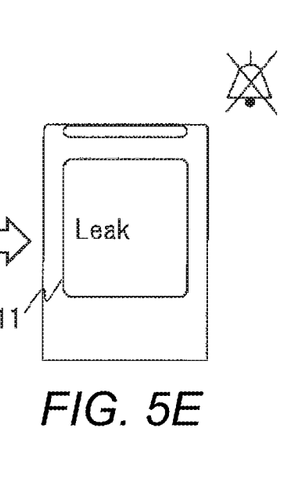

The processor 18 notifies of the information (the second information) indicating the skillfulness of bag ventilation. Specifically, the processor 18 notifies of the information (the second information) by using the display on the display 11, the lighting/blinking of the indicator 12 and/or the indicator 25, the sound output from the speaker 15, or a combination of these sets of information. For example, the processor 18 may perform the notification by causing the indicator 25 to light up in a color indicating the normal state (for example, white) or in a color indicating the abnormal state (for example, yellow). As illustrated in FIG. 5E, characters "Leak" are displayed on the display 11. Specific examples of the display on the display 11 will be described with reference to FIGS. 7A to 7D.

Figure 6:
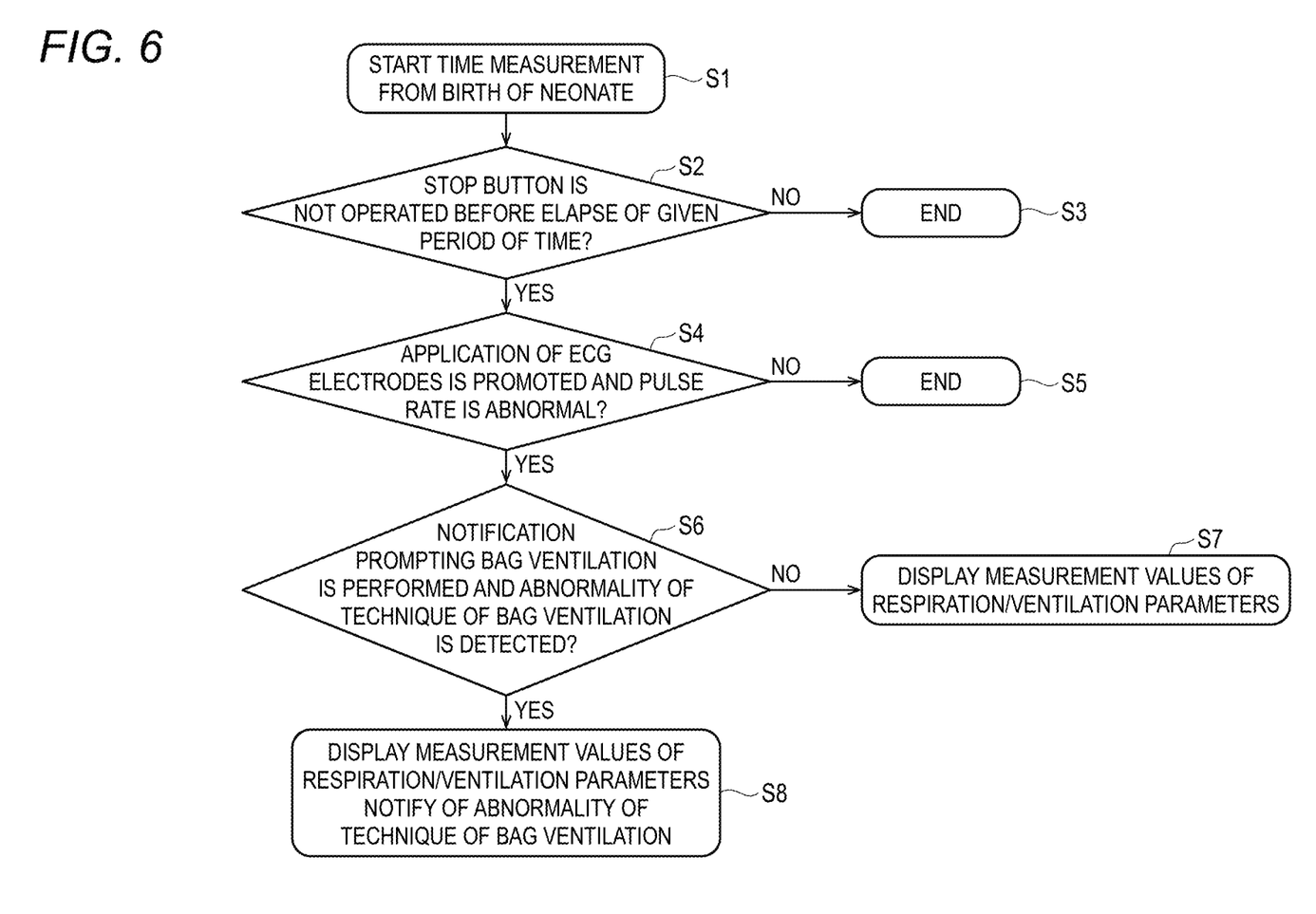
FIG. 6 is a flowchart illustrating the operation of the monitoring device 10 of Embodiment 1.

Then, the operation of the neonate treatment system 1 will be again described with reference to the flowchart of FIG. 6. In the case where a neonate is born, the monitoring device 10 starts the time measurement in response to the pressing of the start button (S1).

In the case where the stop button is pressed before elapse of the given period of time (for example, 20 seconds) (S2: No), the monitoring device 10 determines that the neonate is in a normal respiration state, and ends the process (S3).

In the case where the stop button is not pressed even after passage of the given period of time (S2: Yes), by contrast, the monitoring device 10 performs notification prompting application of the ECG electrodes 30 (notification prompting measurement of the pulse rate), and then measures the pulse rate (S4). If the pulse rate is not abnormal (S4: No), the monitoring device 10 determines that the neonate is in the normal state, and ends the process (S5).

If the pulse rate is abnormal (S4: Yes), the monitoring device 10 notifies of information (the first information) prompting bag ventilation by the ventilation bag 20 (S6). The notification may be performed, for example, by displaying the message of "Perform bag ventilation" on the display 11, or by causing the indicator 12 and/or the indicator 25 to light up (or blink) in a predetermined color.

The monitoring device 10 detects an abnormality of the technique of bag ventilation based on the signal acquired by the sensor 24 which is attached to the ventilation bag 20 (S6). If an abnormality of the technique of bag ventilation is not detected (S6: No), the monitoring device 10 causes the display 11 to display the measurement value of the pulse rate (an example of the first parameter), that of the PIP (an example of the third parameter), that of the ventilation rate (an example of the second parameter), and the like (S7). Measurement values which are displayed on the display 11 are not limited to those above described. Alternatively, the monitoring device 10 may cause the indicator 12 to light up or blink in a color indicating that bag ventilation is normal.

If an abnormality of the technique of bag ventilation is detected (S6: Yes), by contrast, the monitoring device 10 causes the display 11 to display the measurement values of the pulse rate, the PIP, and the ventilation rate (S7). In addition to the above, the monitoring device 10 notifies of information of the skillfulness of bag ventilation (the second information, and, in this case, information informing that the skillfulness of bag ventilation must be improved). The information indicating the skillfulness of bag ventilation may be notified by lighting/blinking/color change of the indicators 12, 25, or a message indicting it may be displayed on the display 11.

Figure 7A:
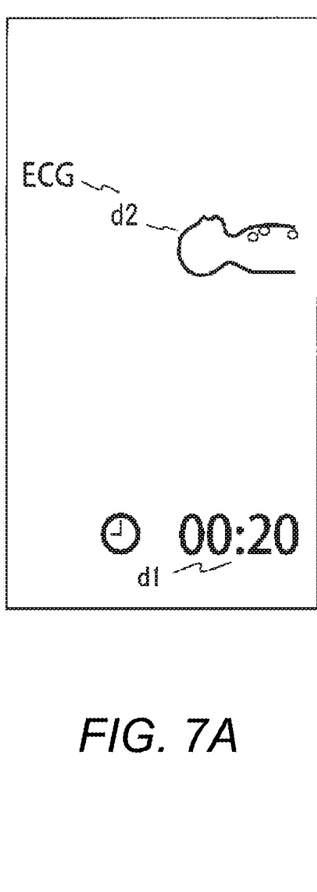
FIGS. 7A to 7D illustrate examples of a display on a display 11 in Embodiment 1.

Then, examples of the display on the display 11 will be described with reference to FIGS. 7A to 7D. FIG. 7A illustrates an example of a display on the display 11 which is performed at 20 seconds after the birth of the neonate. As illustrated, an elapsed time d1 (00:20) after the start event is displayed, and also a display d2 for prompting application of the ECG electrodes 30 is displayed.

Figure 7B:
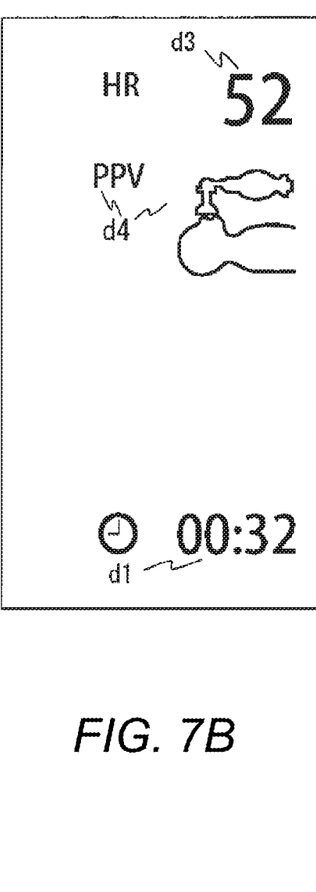

FIG. 7B illustrates an example of a display which is performed after the pulse rate is measured. As illustrated, the elapsed time d1 (00:32) after the start event, d3 (HR=52 bpm) indicating the pulse rate, and d4 (PPV) prompting bag ventilation by the ventilation bag 20 are displayed.

Figure 7C:
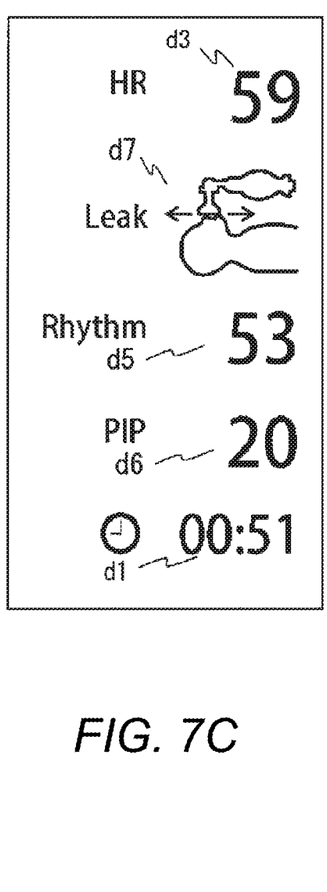

FIG. 7C illustrates a first example of a display which is performed during execution of bag ventilation. The elapsed time d1 (00:51) after the start event, d3 (HR=59 bpm) indicating the pulse rate, d5 (Rhythm=53/min) indicating the ventilation rhythm, and d6 (PIP=20 cmH2O) indicating the measurement value of the PIP are displayed. In addition to the above, d7 indicating that many leaks occur in bag ventilation is displayed.

Figure 7D:
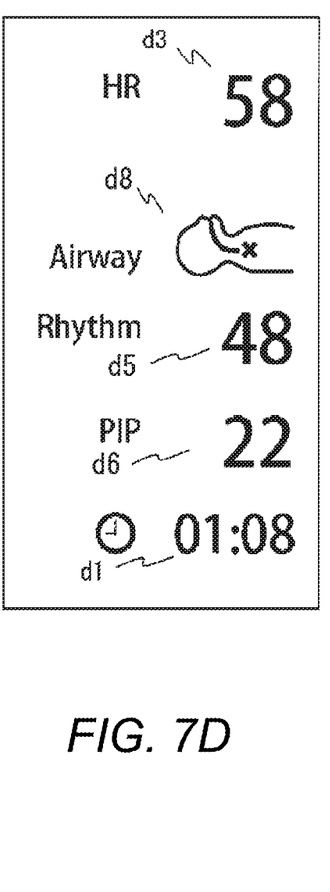

FIG. 7D illustrates a second example of the display which is performed during execution of bag ventilation. The elapsed time d1 (01:08) after the start event, d3 (HR=58 bpm) indicating the pulse rate, d5 (Rhythm=48/min) indicating the ventilation rhythm, and d6 (PIP=22 cmH2O) indicating the measurement value of the PIP are displayed. In addition to the above, d8 indicating airway blockage is displayed.

Then, effects of the neonate treatment system 1 of the embodiment will be described. When the pulse rate (an example of the first parameter) is abnormal, the monitoring device 10 performs notification prompting bag ventilation. This enables bag ventilation to be started at an adequate timing, and the respiration state of the neonate can be rapidly improved.

After bag ventilation is started, the monitoring device 10 notifies of information relating to the skillfulness of bag ventilation (the second information). This enables bag ventilation to be appropriately performed.

The monitoring device 10 notifies of information relating to the skillfulness of bag ventilation by lighting up or blinking of the indicator 25 (the first indicator). In the case where the skillfulness of bag ventilation is notified by the indicator 25 disposed in the ventilation bag 20, when the gaze of the user is simply turned to the hands performing the technique of bag ventilation, it is possible to know the skillfulness.

Moreover, the monitoring device 10 may notify of information relating to the skillfulness of bag ventilation by lighting up or blinking of the indicator 12. According to the configuration, when the gaze of the user is simply turned to the monitoring device 10, it is possible to know the skillfulness of bag ventilation while referring to the display 11 on which other vital signs information is displayed.

In the case where there is no an inputting operation for notifying that the neonate is normal even after passage of the given period of time from the start event, the monitoring device 10 performs notification prompting the measurement of the pulse rate (the first parameter). According to the configuration, the measurement of the pulse rate can be rapidly started, and the neonate can be quickly treated.

(Modification 1)

Then, a modification relating to the lighting up and blinking operations of the indicator 25 will be described. Although, in the above-described embodiment, after bag ventilation is performed, only the skillfulness (the second information) of bag ventilation is notified by lighting up and blinking of the indicators 12, 25, the invention is not limited to this. For example, the processor 18 may transmit, to the ventilation bag 20, an instruction signal which causes at least one of the lighting up or blinking/lighting color/blinking color/blinking speed of the indicator 25 to be changed, in accordance with a combination of the determination of whether the measurement information of the second parameter is abnormal or not, and that of whether the measurement information of the parameter (the third parameter) relating to respiration is abnormal or not. The modification will be described with reference to FIG. 8.

Figure 8:
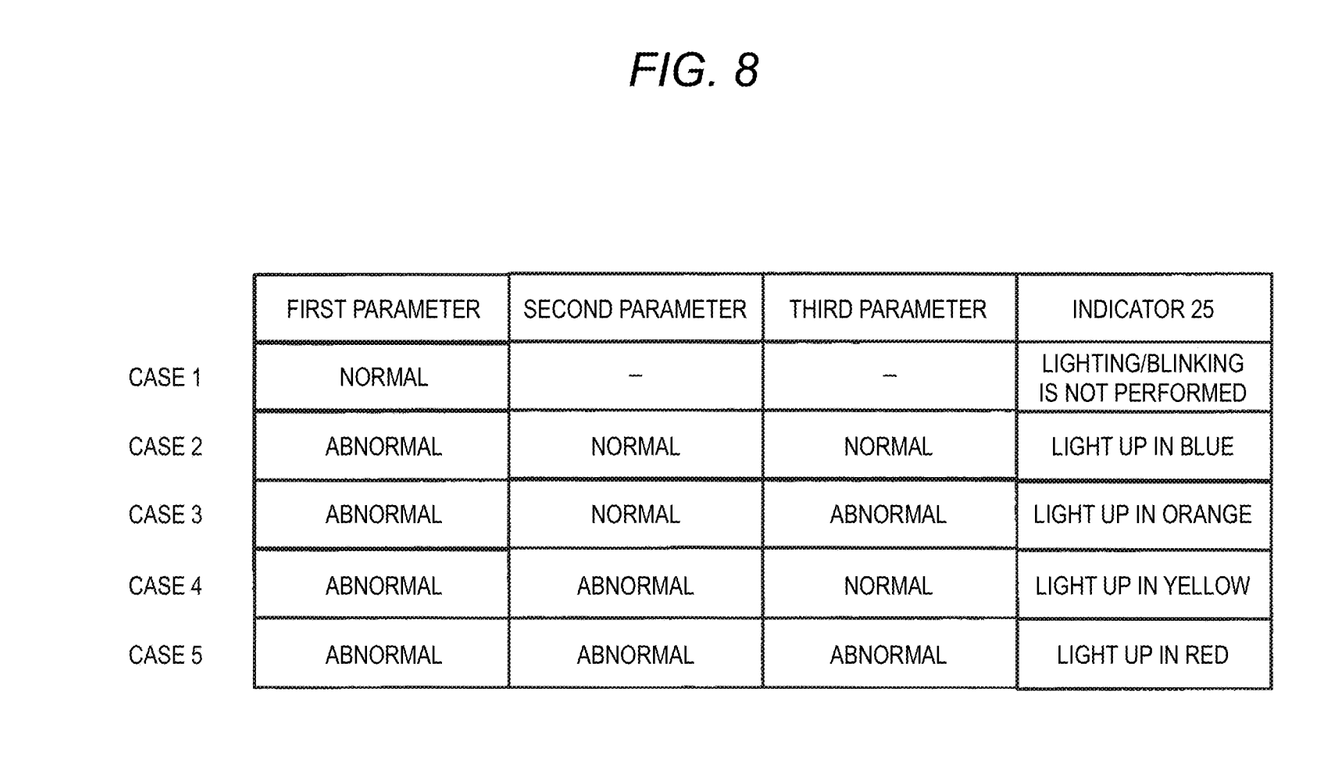
FIG. 8 illustrates an example of a lighting/blinking pattern of an indicator 25 in a modification of Embodiment 1.

In the modification of FIG. 8, in the case where the pulse rate (the first parameter) is normal, the processor 18 does not cause the indicator 25 to light up or blink (Case 1).

In the case where the pulse rate (the first parameter) is abnormal, and the other parameters (the second and third parameters) are normal, the processor 18 causes the indicator 25 to light up in blue (a color indicating that bag ventilation is continuously necessary) (Case 2).

In the case where the pulse rate (the first parameter) and the parameter (the third parameter) relating to respiration are abnormal, the processor 18 causes the indicator 25 to light up in orange (a color indicating that bag ventilation is continuously necessary, and the respiration state is not good) (Case 3).

In the case where the pulse rate (the first parameter) and the parameter (the second parameter) relating to bag ventilation are abnormal, the processor 18 causes the indicator 25 to light up in yellow (a color notifying that bag ventilation is continuously necessary, and the technique of bag ventilation must be improved) (Case 4).

In the case where the all parameters are abnormal, the processor 18 causes the indicator 25 to light up in red (a color notifying that the condition of the neonate is serious, and the technique of bag ventilation must be improved) (Case 5).

In the case where, as described above, the lighting pattern of the indicator 25 is changed by a combination of the measurement information of the parameters, when the user simply gazes the hands performing bag ventilation, the user can know both the body condition of the neonate and the skillfulness of bag ventilation.

(Modification 2)

The processor 18 may cause the indicator 25 to notify of information relating to the skillfulness of bag ventilation, and the indicator 25 to notify of an ideal ventilation speed. For example, the processor designates the information (the second information) indicating the skillfulness of bag ventilation, by the lighting color of the indicator 25, and transmits an instruction signal designating the ideal timing of bag ventilation by means of the blinking timing, to the ventilation bag 20. In response to this, the indicator 25 blinks in a lighting color and timing which are designated. The ideal timing of bag ventilation may be set by default, or may be set through the operation interface 14.

In the case where the state is where the technique of bag ventilation is not required to be improved, specifically, the processor 18 causes the indicator 25 to light up in white (the color indicating that the technique of bag ventilation is normal), and to blink at the ideal ventilation speed. In the case where the state is where the technique of bag ventilation is required to be improved, by contrast, the processor 18 causes the indicator 25 to light up in yellow (the color indicating that the technique of bag ventilation is abnormal), and to blink at the ideal ventilation speed.

Therefore, the user can know the ideal ventilation speed together with the skillfulness of the technique of bag ventilation.

(Modification 3)

A modification relating to the lighting/blinking controls of the indicators 12, 25 will be described. In the modification, it is assumed that information notified by the indicator 12 is different from that notified by the indicator 25.

In the modification, the indicator 25 is used only for notifying of the information (the second information) indicating the skillfulness of bag ventilation. The processor 18 calculates the information indicating the skillfulness of bag ventilation, by using the above-described method. In the case where the technique of bag ventilation is not required to be improved, the processor 18 does not cause the indicator 25 to light up or blink (or causes the indicator to light up in white (which is the color indicating that the technique is normal). In the case where the technique of bag ventilation is required to be improved, by contrast, the processor 18 causes the indicator 25 to light up in, for example, yellow.

On the other hand, the indicator 12 is used for notifying of the measurement information (measurement values and waveforms) of the vital signs. The vital signs include the pulse rate (the measurement information of the first parameter) and the parameter (the third parameter) relating to the respiration such as the PIP. In the case where the measurement information of the vital signs is abnormal, the processor 18 causes the indicator to light up or blink in a color attracting attention such as red.

According to the configuration, information of the skillfulness of bag ventilation, and the condition of the neonate can be correctly notified while distinguishing the information and the condition from each other. The above-described notification patterns (the lighting colors) are mere examples, and the processor 18 is requested to change at least one of lighting or blinking/lighting color/blinking color/blinking speed of the indicator 25, thereby notifying of information of the skillfulness of bag ventilation, and the condition of the neonate while distinguishing them from each other.

Although, in the above, the invention conducted by the inventors has been specifically described based on the embodiment, the presently disclosed subject matter is not limited to the above-described embodiment, and it is a matter of course that various changes can be made without departing from the scope of the presently disclosed subject matter.

In the above description, for example, the pulse rate is detected based on the vital signs signals acquired from the ECG electrodes 30. The presently disclosed subject matter is not limited to this. The monitoring device 10 may be connected with an arbitrary sensor (the first sensor) which acquires measurement information of a parameter derived from a heart rate. For example, a SpO2 probe may be connected to the monitoring device 10, and the pulse rate may be calculated based on the pulse waveform. The parameter is not limited to the pulse rate, and the monitoring device 10 may perform notification prompting ventilation by the ventilation bag 20 based on measurement information (measurement values and waveforms) of other parameters (such as the heart sound) derived from the heart rate.

As described above, the ventilation bag 20 is an example of the ventilation medical apparatus, and may be a T-piece connected to an insufflation pressure source. In the case where a T-piece is used in place of the ventilation bag 20, the T-piece has a configuration which is identical with or similar to that of the sensor 24 or the indicator 25, and therefore a knob for adjusting the air (the gas) to be sent to the neonate, and the like. Also in this case, the T-piece and the monitoring device 10 may be requested to perform operations which are similar to or same as the described above configuration.

For example, the monitoring device 10 performs notification prompting measurement of the pulse rate, after an elapsed given time from the start event, and, when an abnormality of the pulse rate is detected, performs notification prompting ventilation by the T-piece. Also with respect to the skillfulness of ventilation by a T-piece (for example, an abnormality of the ventilation amount due to inadequateness of a setting of the ventilation amount which has been conducted by dial setting), the notification may be performed through the indicator 25 disposed in the T-piece. Even in this case (not in bag ventilation, but in ventilation by the T-piece), when such notification is performed, the user can know the adequateness of the ventilation which is performed by using the T-piece.

Although, in the above, the description has been made under assumption that the neonate treatment system 1 mainly treats a neonate who has been just born, the presently disclosed subject matter may be applied to condition management of, for example, an infant. Namely, the neonate treatment system 1 is a mode of the patient treatment system. Even in the case where an infant is targeted, the monitoring device 10 and the ventilation bag 20 may operate in a substantially same or similar manner as the above-described operation.

What is claimed is:

1. A patient treatment system comprising:
   a ventilation medical apparatus that applies positive pressure ventilation to a patient,
   a monitoring device configured to be connected to the ventilation medical apparatus,
   a first sensor configured to measure a first parameter derived from a heart rate of the patient,
   wherein the monitoring device is configured to receive the first parameter derived from the first sensor, from a signal of a first sensor which is connected to the monitoring device, and, when an abnormality of measurement information of the first parameter is detected, the monitoring device is configured to notify of a first information regarding ventilation by the ventilation medical apparatus,
   wherein the ventilation medical apparatus includes a first indicator which is configured to light up or blink to notify of the first information in response to an instruction signal from the monitoring device, and
   wherein, after the notification of the first information, the monitoring device is configured to notify of a second information indicating skillfulness of ventilation detected based on a second signal which is sent from a second sensor disposed in the ventilation medical apparatus.

2. The patient treatment system according to claim 1, wherein
   the monitoring device is configured to transmit an instruction signal notifying of the second information to the ventilation medical apparatus, and causes the first indicator to light up or blink.

3. The patient treatment system according to claim 2, wherein the monitoring device is configured to:
calculate measurement information of a second parameter relating to ventilation that is calculated based on the second signal which is acquired from the second sensor, and
calculate measurement information of a third parameter relating to respiration that is calculated based on a vital signs signal which is acquired from the second sensor, and
transmit the instruction signal for changing at least one of lighting up or blinking/lighting color/blinking color/blinking speed of the first indicator based on a combination of whether the measurement information of the second parameter is abnormal or not, and whether the measurement information of the third parameter is abnormal or not.

4. The patient treatment system according to claim 2, wherein the monitoring device is configured to transmit the instruction signal to the ventilation medical apparatus, the instruction signal designating the second information by means of a lighting color of the first indicator, and designating an ideal timing of ventilation by means of a blinking timing of the second indicator.

5. The patient treatment system according to claim 1, wherein the monitoring device has a second indicator on a housing, and the monitoring device is configured to cause the second indicator to light up or blink, thereby notifying of the first information.

6. The patient treatment system according to claim 1, wherein
the monitoring device has a second indicator which is configured to light up or blink, on a housing,
the monitoring device is configured to transmit an instruction signal notifying of the second information, to the ventilation medical apparatus, thereby causing the first indicator to light up or blink, and
the monitoring device is configured to cause the second indicator to light up or blink, based on measurement information of vital signs which is calculated from the first parameter that is supplied to the monitoring device.

7. The patient treatment system according to claim 1, wherein the input of informing of a normality of the patient is received by a user touching a button on a touch screen.

8. The patient treatment system according to claim 7, wherein,
after an elapse of a given time period from a start event, there is no input informing of the normality of the patient, the monitoring device is configured to output a first alarm sound, and,
in a case where measurement information of the first parameter is abnormal, the monitoring device outputs a second alarm sound.

9. The patient treatment system according to claim 1, wherein
the monitoring device is configured to calculate measurement information of a second parameter relating to ventilation based on the signal which is sent from the second sensor, and calculates the second information based on the measurement information of the second parameter.

10. The patient treatment system according to claim 1, wherein
the monitoring device has a display on a housing, and the monitoring device is configured to display, on the display, the measurement information of the first parameter, a measurement information of a second parameter relating to ventilation that is calculated based on the signal which is acquired from the second sensor, and a measurement information of a third parameter relating to respiration that is calculated based on a vital signs signal which is acquired from the second sensor.

11. The patient treatment system according to claim 1, wherein the ventilation medical apparatus is a positive pressure ventilation device.

12. The patient treatment system according to claim 11, wherein the positive pressure ventilation device includes an Ambu bag, a Jackson Rees bad, a flow inflating bag, a bag valve mask, or T-piece.

13. A monitoring device configured to be connectable to a ventilation medical apparatus that applies positive pressure ventilation on a patient, the monitoring device comprising:
a display;
a receiver configured to receive data from a sensor configured to measure a first parameter derived from a heart rate of a patient; and
a controller configured to receive the first parameter derived from the sensor which is connected to the monitoring device via the receiver, and when an abnormality of measurement information of the first parameter is detected, the controller is configured to display, on the display, a first information regarding ventilation by the ventilation medical apparatus,
wherein the ventilation medical apparatus includes a first indicator which is configured to light up or blink to notify of the first information in response to an instruction signal from the monitoring device, and
wherein, after the display of the first information, the monitoring device is configured to display a second information indicating skillfulness of ventilation detected based on a second signal which is sent from a second sensor disposed in the ventilation medical apparatus.

14. A patient treatment system comprising:
a ventilation medical apparatus that applies positive pressure ventilation to a patient,
a monitoring device configured to be connected to the ventilation medical apparatus,
a first sensor configured to measure a first parameter derived from a heart rate of a patient,
wherein the monitoring device is configured to receive the first parameter derived from the first sensor, from a signal of a first sensor which is connected to the monitoring device, and, when an abnormality of measurement information of the first parameter is detected, the monitoring device is configured to notify of a first information regarding ventilation by the ventilation medical apparatus,
wherein the ventilation medical apparatus includes a first indicator which is configured to light up or blink to notify of the first information in response to an instruction signal from the monitoring device, and
wherein the monitoring device is configured to change a mode of light up or blink of the first indicator, based on a combination of whether the measurement information of the first parameter is abnormal or not and whether measurement information of a second parameter relating to respiration is abnormal or not, the second parameter being calculated based on a signal obtained from a second sensor disposed in the ventilation medical apparatus.

* * * * *